United States Patent
Small et al.

[11] Patent Number: 6,063,638
[45] Date of Patent: May 16, 2000

[54] WET CHEMICAL OXIDATION TECHNIQUE AND APPARATUS FOR WATER IMPURITY

[75] Inventors: Robert A. Small; Walter J. Gaylor, both of Seabrook, Tex.

[73] Assignee: Small Family 1992 Revocable Trust, League City, Tex.

[21] Appl. No.: 09/161,058

[22] Filed: Sep. 25, 1998

Related U.S. Application Data

[60] Provisional application No. 60/059,957, Sep. 25, 1997.

[51] Int. Cl.$^7$ .................................................. G01N 33/00
[52] U.S. Cl. ........................... 436/146; 422/80; 422/68.1; 422/78; 422/186.3; 422/79; 422/193; 436/145; 436/181; 210/205
[58] Field of Search ............................... 422/63, 67, 68.1, 422/74, 78, 79, 80, 186.3, 189, 193, 103; 210/205; 436/145, 146, 181

[56] References Cited

U.S. PATENT DOCUMENTS

| | | |
|---|---|---|
| 3,840,341 | 10/1974 | Rogers . |
| 4,277,438 | 7/1981 | Ejzak ........................................ 422/80 |
| 5,132,094 | 7/1992 | Godec .................................... 422/68.1 |
| 5,244,478 | 9/1993 | Jolly . |
| 5,292,666 | 3/1994 | Fabinski ................................ 436/114 |
| 5,312,756 | 5/1994 | Jolly . |
| 5,413,763 | 5/1995 | Jeffers . |
| 5,564,105 | 10/1996 | Alvino . |
| 5,720,889 | 2/1998 | McBrayer . |
| 6,007,777 | 12/1999 | Purcell ..................................... 422/80 |

*Primary Examiner*—Jill Warden
*Assistant Examiner*—Huan Tran
*Attorney, Agent, or Firm*—James L. Jackson; Mayor, Day, Caldwell & Kenton, L.L.P.

[57] ABSTRACT

Apparatus and processes for water impurity analysis and for impurity analysis of various other liquids as well. More particularly, the present invention concerns apparatus and processes for chemical oxidant and catalyst enhanced total organic carbon analysis of liquid samples for determination of the level of organic contamination of the samples. In particular the present invention concerns a novel reactor for TOC anlysis in which carbon, particularly organic carbon is oxidized to $CO^2$ gas for further measurement by a $CO_2$ gas detector, preferably a non-dispersive infrared analyzer. The invention also concerns a process for TOC analysis wherein by measuring the $CO_2$ gas created by combining carbon with oxygen (either in the water, with a carrier gas of oxygen ($O^2$), or a chemical oxidant, such as sodium persulfate, the carbon in the water sample is determined. A process and apparatus are employed for TOC analysis in which UV light having a wave length in the range of from about 3.8 to about 4.3 nanometers is impinged upon a water sample containing chemical oxidants such as Ti $O_2$ or sodium persulfate or both and liberated gas including $CO_2$ is measured by a non-dispersive infrared analyzer.

5 Claims, 1 Drawing Sheet

WET CHEMICAL OXIDATION TECHNIQUE AND APPARATUS FOR WATER IMPURITY

Applicants hereby claim the benefit of Provisional Application Serial No. 60/059,957, filed on Sep. 25, 1997 by Robert A. Small and Walter J. Gaylor and entitled Wet Chemical Oxidation Technique and Apparatus for water Impurity, which is incorporated by reference herein for all purposes.

BACKGROUND OF THE INVENTION

1. Field of the Invention

This invention relates generally to apparatus and processes for water impurity analysis and to impurity analysis of various other liquids as well. More particularly, the present invention concerns apparatus and processes for chemical oxidant and catalyst enhanced total organic carbon analysis of liquid samples for determination of the level of organic contamination of the samples.

2. Description of the Prior Art

In many industrial and laboratory situations an authoritative test is needed for determining the degree of pollution that exists in a liquid, particularly water, stream. Water pollution due to the presence of organic materials has been measured indirectly in BOD analysis by how actively bacteria will use up the organic material in a given sample and consume oxygen from the sample. Since BOD analysis is an exceedingly slow procedure, it has been determined to be more appropriate to measure liquid samples directly for contamination due to the presence and volume of organic materials and to provide a system for rapid and low cost sample analysis. A low cost and rapid analysis process known as Total organic carbon (TOC) analysis has proven quite acceptable for this purpose. Moreover, TOC data can be readily converted to BOD or COD data if desired.

TOC analysis is typically conducted by injecting a known volume of water or other liquid into a furnace containing acid coated quartz chips and being at a sufficient temperature, 150° C., for example, to convert the inorganic carbon in the sample to $CO_2$ which is then measured by an infrared analyzer that is sensitive to $CO_2$. Another like volume from the same sample is then injected into a high temperature furnace, 950° C. for example, containing a catalyst to aid complete combustion. Oxygen is then metered into a reaction tube causing the total carbon, inorganic and organic, to be converted into $CO_2$. The volume of the $CO^2$ within the sample is then measured by an infrared analyzer. The $CO_2$ generated by complete combustion is directly proportional to the total carbon in the sample stream. A problem with TOC analysis of this nature is that inaccuracies can result from the coordination of two separate measurements, especially if the ratio of inorganic carbon content of the sample as compared to total carbon is large. The use of a catalyst can also create some problems from the standpoint of accuracy of the TOC analysis being performed.

More recently, TOC analyzer manufacturers have introduced analyzers using a low-temperature ultra-violet (UV) promoted chemical oxidation method which offers certain advantages over combustion TOC analysis. These systems measure TOC directly be means of an acidification and scrubbing pretreatment system which removes carbonates prior to oxidation. The feasibility of the UV/persulfate technique for oxidizing organic carbon was demonstrated a number of years ago and is well documented relative to its excellent oxidation efficiency. The major advantage of a low temperature UV promoted chemical TOC system is that all reactions take place in the liquid phase, resulting in increased reliability and reduced TOC analyzer maintenance requirements.

Total organic carbon analysis is often considered beneficial as a rapid screening method to determine requirements of more costly and time-consuming specific toxic and other organic component analyses. In many cases, depending upon the application, TOC analysis is an adequate and inexpensive substitute for more time consuming and more expensive alternative methods for determination of water quality, provided the TOC analyzer being employed has sufficient sensitivity and capability. These more time consuming and expensive water quality determination methods, for example, include among others, the biochemical oxygen demand (BOD) test and the chemical oxygen demand (COD) test.

It has been determined that titanium dioxide ($Ti\ O_2$) is a superior catalyst to aid in the oxidation of organic carbon in water, even at room temperatures, without the aid of any other chemical oxidant. Further enhancement of the carbon oxidation process is accomplished by the use of ultraviolet light impinging on the water sample, typically in the range of from about 3.8 to about 4.3 nanometers. Even further oxidation is accomplished by the chemical addition of sodium persulfate.

It is thus an important feature of the present invention to provided a novel process and apparatus for TOC analysis by which UV light of proper wave length is impinged upon a water sample containing chemical oxidants such as $Ti\ O_2$ or sodium persulfate or both.

It is also a feature of the present invention to provide a novel reactor for TOC analysis in which carbon, particularly organic carbon is oxidized to $CO_2$ gas for further measurement by a $CO^2$ gas detector, preferably a non-dispersive infrared analyzer.

It is an even further feature of the present invention to provide a novel process for TOC analysis wherein by measuring the $CO_2$ gas created by combining carbon with oxygen (either in the water, with a carrier gas of oxygen ($O_2$), or a chemical oxidant, such as sodium persulfate, the carbon in the water sample is determined. Other and further features of the present invention will become obvious and inherent upon review of this disclosure and are considered to be incorporated within the spirit and scope of the present invention.

BRIEF DESCRIPTION OF THE DRAWINGS

So that the manner in which the above recited features, advantages and objects of the present invention are attained and can be understood in detail, a more particular description of the invention, briefly summarized above, may be had by reference to the preferred embodiment thereof which is illustrated in the appended drawings, which drawings are representative of a preferred embodiment of this invention and are incorporated as a part hereof.

It is to be noted however, that the appended drawings illustrate only a typical embodiment of this invention and are therefore not to be considered limiting of its scope, for the invention may admit to other equally effective embodiments.

In the Drawings:

Figure 1:
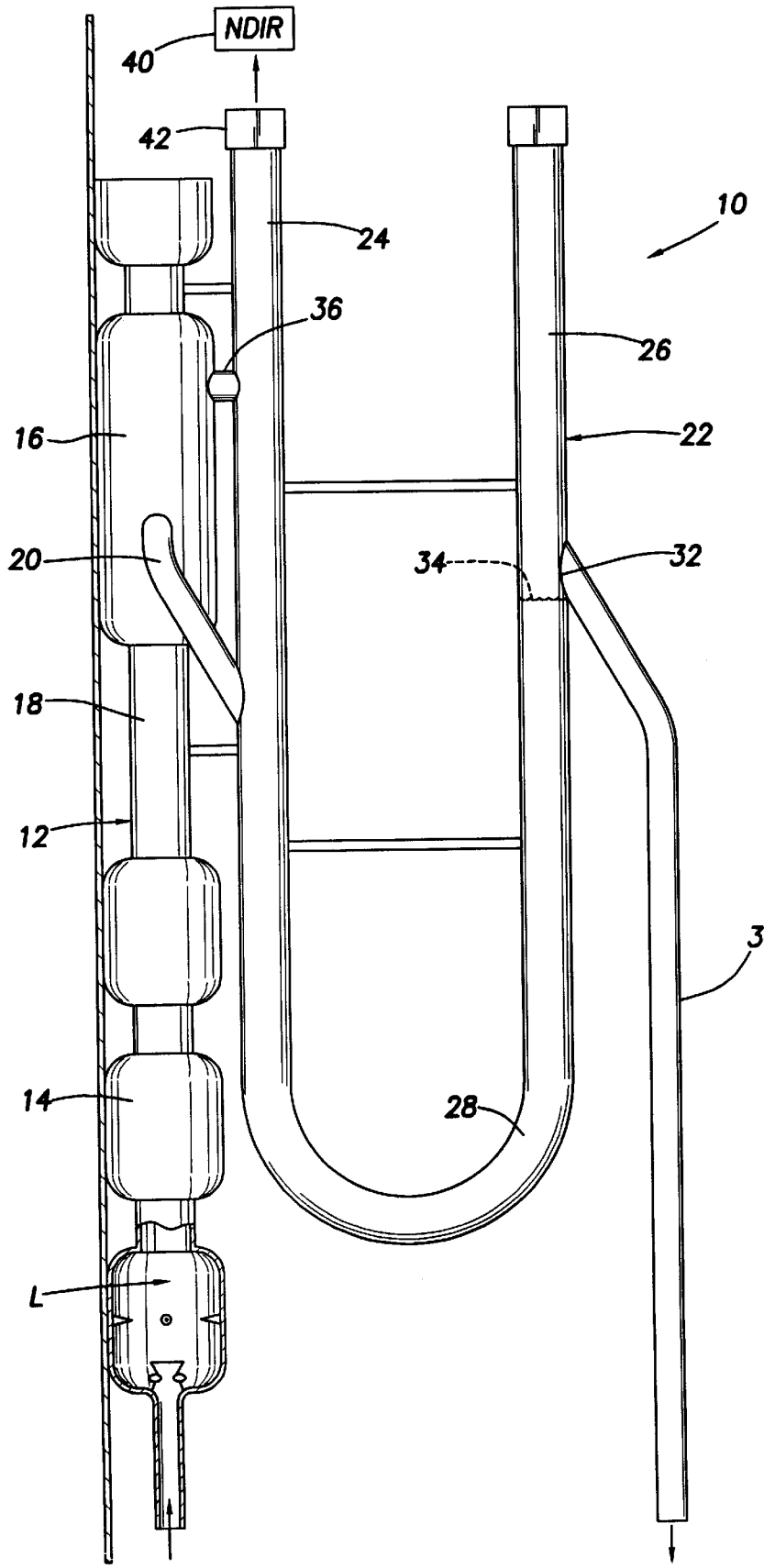

The single FIGURE of the drawings is an elevational view of a TOC reactor and analyzer constructed in accordance with the principles of the present invention and representing the preferred embodiment of the invention.

DETAILED DESCRIPTION OF PREFERRED EMBODIMENT

Referring now to the single FIGURE of the drawings, a total organic carbon (TOC) analyzer, constructed according with the principles of the present invention, is shown generally at 10 and incorporates a main reactor body generally at 12 having a lower section 14 and an upper section 16. A fluid sample supply tube 18 is connected and sealed to the bottom of the lower reactor section 14 to provide for introduction of a sample stream into the reactor. The main reactor body also incorporates a light source shown generally at "L" by which the sample is radiated with ultraviolet light. The ultraviolet light source is preferably in the form of a quartz encapsulated ultraviolet light. At least some of the sample is vaporized in the lower reactor section, liberating a vapor or gaseous phase which traverses an intermediate tubular section 18 of the reactor.

The upper reactor section 16 is a condenser section wherein the vapor phase of the water sample will condense, causing waste and $CO_2$ gas to exit the reactor via a drain tube 20, descending into a U-shaped tubular condensate and gas receiver shown generally at 22. The condensate and gas receiver 22 defines a pair of spaced, generally parallel gas collection sections 24 and 26 and a liquid condensate collection trap 28. A waste drain tube 30 is connected to the gas collection section 26 at 32 to drain away liquid waste and to ensure that the liquid level within the condensate and gas receiver 22 does not exceed level 34.

At the upper portion of the condenser section 16 a gas connector 36 connects the condenser section with the upper portion of the gas collection section 24. An infrared analyzer, such as a non-dispersive infrared analyzer 40 is provided to receive $CO_2$ gas that is discharged from the upper end 42 of the gas collection section 24 of the reactor.

The resulting TOC reactor/analyzer typically operates at ambient temperature and does not require high temperature for complete oxidation of a liquid sample. Since a high temperature oven or reactor is not needed, the cost of the TOC analyzer can be quite low and the cost of TOC analysis can be quite low as well. The safety of the TOC analyzer unit is also materially enhanced by eliminating the need for apparatus for maintaining high temperatures The reactor apparatus can be of quite small construction, thereby permitting it to be effectively utilized in small water quality testing facilities and permitting a TOC analyzer system to be produced in portable form for transport to test sites.

In view of the foregoing it is evident that the present invention is one well adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive, the scope of the invention being indicated by the claims rather than the foregoing description, and all changes which come within the meaning and range of equivalence of the claims are therefore intended to be embraced therein.

We claim:

1. A reactor system for accomplishing total organic carbon analysis of a liquid sample, comprising:
   (a) a main reactor body adapted for vertical orientation and having a lower reactor section having a liquid sample inlet at the lower end thereof, said main reactor body having an upper reactor section, said upper and lower reactor sections being interconnected by an intermediate tubular reactor section;
   (b) an ultraviolet light source being located within said main reactor body and adapted for ultraviolet radiation of the liquid sample therein;
   (c) a U-shaped tubular waste liquid and gas receiver having a pair of generally parallel tubular elements for receiving liberated $CO_2$ from the liquid sample;
   (d) liquid waste and $CO_2$ drain means interconnecting said upper reactor section with one of said generally parallel tubular elements to transfer waste liquid and $CO_2$ into said U-shaped tubular waste liquid and gas receiver;
   (e) an infrared analyzer; and
   (f) one of said pair of generally parallel tubular elements conducting $CO_2$ to said infrared analyzer for measuring the total carbon content of the liquid sample.

2. The reactor system of claim 1, wherein:
   a liquid waste drain being connected intermediate one of said generally parallel tubular elements for draining away liquid waste and for establishing a liquid gas interface level to permit the existence of sufficient gas space for collection of $CO_2$ from the liquid sample.

3. The reactor system of claim 1, wherein:
   said infrared analyzer being a non-dispersive infrared analyzer.

4. The reactor system of claim 1, wherein:
   one of said generally parallel tubular elements having gas transferring connection with said upper reactor section.

5. The reactor system of claim 1, wherein:
   one of said generally parallel tubular elements having gas transferring connection with said upper reactor section at a location above said liquid waste and $CO_2$ drain means.

* * * * *